(12) United States Patent
Barror et al.

(10) Patent No.: US 8,956,712 B2
(45) Date of Patent: Feb. 17, 2015

(54) SOLID STATE POWER SOURCE WITH FRAMES FOR ATTACHMENT TO AN ELECTRONIC CIRCUIT

(71) Applicants: Infinite Power Solutions, Inc., Littleton, CO (US); Medtronic, Inc., Minneapolis, MN (US)

(72) Inventors: Michael W. Barror, Minneapolis, MN (US); John K. Day, Minneapolis, MN (US); Shawn W. Snyder, Golden, CO (US); Alexandra Z. LaGuardia, Denver, CO (US); Damon E. Lytle, Golden, CO (US); Bernd J. Neudecker, Littleton, CO (US)

(73) Assignees: Medtronic, Inc., Minneapolis, MN (US); Sapurast Research LLC, Wilmington, DE (US)

(*) Notice: Subject to any disclaimer, the term of this patent is extended or adjusted under 35 U.S.C. 154(b) by 95 days.

(21) Appl. No.: 13/692,729

(22) Filed: Dec. 3, 2012

(65) Prior Publication Data

US 2014/0154553 A1    Jun. 5, 2014

(51) Int. Cl.
*H01M 2/18*    (2006.01)
*H01M 2/02*    (2006.01)
(Continued)

(52) U.S. Cl.
CPC .............. *H01M 2/0202* (2013.01); *A61N 1/378* (2013.01); *H01M 10/0436* (2013.01);
(Continued)

(58) Field of Classification Search
CPC .............. A61N 1/378; H01M 10/0436; H01M 10/056; H01M 2/0202; H01M 6/181; H01M 2/0267; H01M 2/0292; H01M 10/0486

USPC ......... 429/121, 129, 130, 138, 163, 167, 168, 429/169, 173
See application file for complete search history.

(56) References Cited

U.S. PATENT DOCUMENTS 5,665,490 A    9/1997    Takeuchi et al.
8,044,508 B2   10/2011   Jenson et al.
(Continued)

FOREIGN PATENT DOCUMENTS

EP       1841001 A1    10/2007
EP       2251922 A1    11/2010
WO   WO-2007011900 A1    1/2007

OTHER PUBLICATIONS

PCT International Search Report and Written Opinion (dated Jun. 26, 2014), International Application No. PCT/US2013/072750, International Filing Date-Dec. 3, 2013, (12 pages).

*Primary Examiner* — Patrick Ryan
*Assistant Examiner* — Ben Lewis
(74) *Attorney, Agent, or Firm* — Blakely, Sokoloff, Taylor & Zafman LLP

(57) ABSTRACT

A power source for a solid state device includes: a first frame having a first contact portion, a first bonding portion and a first extension portion between the first contact portion and the first bonding portion; a second frame having a second contact portion, a second bonding portion and a second extension portion between the second contact portion and the second bonding portion; and a first pole layer, an electrolyte layer and a second pole layer positioned between the first and second contact portions, wherein a first portion of the electrolyte layer is positioned between the first extension and the first pole and a second portion of the electrolyte layer is positioned between the first extension and the second pole.

10 Claims, 15 Drawing Sheets

(51) Int. Cl.
*A61N 1/378* (2006.01)
*H01M 10/04* (2006.01)
*H01M 10/056* (2010.01)
*H01M 6/18* (2006.01)

(52) U.S. Cl.
CPC ........... *H01M 10/056* (2013.01); *H01M 6/181* (2013.01); *H01M 2/0267* (2013.01); *H01M 2/0292* (2013.01); *H01M 10/0486* (2013.01)

USPC ........... 428/138; 429/121; 429/129; 429/130; 429/163; 429/167; 429/168; 429/169; 429/173

(56) References Cited

U.S. PATENT DOCUMENTS

2007/0015060 A1* 1/2007 Klaassen .................. 429/309
2011/0123868 A1   5/2011 Kawaoka et al.

* cited by examiner

SOLID STATE POWER SOURCE WITH FRAMES FOR ATTACHMENT TO AN ELECTRONIC CIRCUIT

BACKGROUND OF THE INVENTION

1. Field of the Invention

The embodiments of the invention relate to a solid state power source, and more particularly, for example, to a solid state power source with frames for attachment to an electronic circuit. Although embodiments of the invention are suitable for a wide scope of applications, it is particularly suitable for powering an electronic circuit in an implant device in which both the solid state power source and the electronic circuit are hermetically sealed in an enclosure.

2. Discussion of the Related Art

In general, a conventional type of solid state power source includes a metallic battery encasement surrounding the bare structure of an electrochemical cell. The metallic battery encasement can include top and bottom metal shells, which are insulated from one another. The sides of the electrochemical cell are each respectively contacted by one of the top and bottom metal shells. An electrochemical cell can be a component having a positive cathode on one side, a negative anode on the other side, and an electrolyte between the cathode and anode. Solid state power sources with such a structure are often referred to as either coin or button cells.

The conventional attachment architectures for conventional types of solid state power devices typically have some sort of compression contact mechanism and a battery holder mounted on the electronic circuitry for retaining and contacting the coin or button cell to electronic circuitry. However, such a battery holder with the button or coin cell fixated into a metal spring clip in turn consumes premium volume/space. That is, the volume of a conventional implementation of a component containing an electrochemical cell, including the battery holder, the external compression contact mechanism, and the metallic battery encasement, can be twice or three times as much as the volume of the bare structure of an electrochemical cell.

Solid state power sources that are hermetically sealed into a housing of an electronic device, for example, facilitate the advancements in miniaturization of the implantable medical devices. It is desirable to reduce the device size so that the overall circuitry can be more compact. Moreover, the miniaturization of implantable medical devices is driving size and cost reduction of all implantable medical devices components including the electronic circuitry.

Conventional techniques that lead to successful miniaturization of implantable enclosures included: a) minimizing the electronic circuitry of the sensor(s), monitors(s) and/or actuator(s); b.) minimizing the power source(s); and/or c) minimizing the attachment architecture of the power source(s) to the electronic circuitry. A power source having conventional attachment architectures along with the metallic battery encasement can take up the largest part of implantable enclosures. Of course, the volume of the power source is most useful in a component containing an electrochemical cell. However, the use of premium volume/space on spring clips as well as other auxiliary battery holder/encasement materials can be unacceptable, up to the point where an implantable enclosure with a specific type of electronic circuitry may not make sense with regard to particular applications (e.g. medical), such as those with severe space or size limitations.

SUMMARY OF THE INVENTION

Accordingly, embodiments of the invention are, for example, directed to a solid state power source with frames for attachment to an electronic circuit that substantially obviates one or more of the problems due to limitations and disadvantages of the related art.

An object of embodiments of the invention is to provide a direct mechanical and electrical attachment architecture for an electrochemical cell to the electronic circuitry of an implantable device, which are then both sealed into an air and fluid tight enclosure.

Another object of embodiments of the invention is to position a bare electrochemical cell next to unprotected electronic circuitry within an air tight and fluid tight enclosure.

Another object of embodiments of the invention is to provide a solid state electrochemical cell that includes an electrolyte that provides encapsulation and bonding of an electrochemical cell on frames to enable attachment of the frames to electronic circuitry under ambient air conditions.

Another object of embodiments of the invention is to provide an electrochemical cell on frames with an attachment architecture having both terminals mechanically and electrically connected to an electronic circuit located on one side of the electrochemical cell.

Another object of embodiments of the invention is to provide more than one solid state electrochemical cell in the same attachment architecture connected in parallel to electronic circuitry.

Additional features and advantages of embodiments of the invention will be set forth in the description which follows, and in part will be apparent from the description, or may be learned by practice of embodiments of the invention. The objectives and other advantages of the embodiments of the invention will be realized and attained by the structure particularly pointed out in the written description and claims hereof as well as the appended drawings.

To achieve these and other advantages and in accordance with the purpose of embodiments of the invention, as embodied and broadly described, the solid state power source includes a first frame having a first contact portion, a first bonding portion and a first extension portion between the first contact portion and the first bonding portion; a second frame having a second contact portion, a second bonding portion and a second extension portion between the second contact portion and the second bonding portion; and a first pole layer, an electrolyte layer and a second pole layer positioned between the first and second contact portions, wherein a first portion of the electrolyte layer is positioned between the first extension and the first pole and a second portion of the electrolyte layer is positioned between the first extension and the second pole.

In another aspect, a power source for a solid state device includes a first frame having a first contact portion, a first bonding portion and a first extension portion between the first contact portion and the first bonding portion; a second frame having a second contact portion, a second bonding portion and a second extension portion between the second contact portion and the second bonding portion; first and second side encapsulant regions positioned between the first and second contact portions, and a first pole layer, a first electrolyte layer and a second pole layer positioned between the first and second contact portions, and between the first and second side encapsulant regions.

In another aspect, a power source for a solid state device includes a first frame having a first contact portion, a first bonding portion and a first extension portion between the first contact portion and the first bonding portion; a second frame having a second contact portion, a second bonding portion and a second extension portion between the second contact portion and the second bonding portion; a first pole layer, an electrolyte layer and a second pole layer positioned between the first and second contact portions; and an encapsulant between the first and second contact portions, wherein the first and second bonding portions are aligned in a first direction and the first and second contact portions are aligned in the first direction.

In another aspect, a device includes: a substrate having a first side and a second side; an electronic circuit on the first side of the substrate; a first frame and a second frame; a first side encapsulant region and a second side encapsulant region positioned between the first and second frames; a first battery having a first pole layer, a first electrolyte layer and a second pole layer positioned between the first and second frames, and between the first and second side encapsulant regions, wherein the first and second frames electrically and mechanically contact the electronic circuit on the first side of the substrate.

It is to be understood that both the foregoing general description and the following detailed description are exemplary and explanatory and are intended to provide further explanation of embodiments of the invention as claimed.

BRIEF DESCRIPTION OF THE DRAWINGS

The accompanying drawings, which are included to provide a further understanding of embodiments of the invention and are incorporated in and constitute a part of this specification, illustrate embodiments of the invention and together with the description serve to explain the principles of embodiments of the invention.

FIG. 6a is a detailed cross-sectional view of an embodiment at section A in FIG. 5a.

FIG. 7a a cross-sectional view along lines B-B' of the embodiment in FIG. 5a.

FIG. 8a is a detailed cross-sectional view of section C of the embodiment in FIG. 5a.

FIG. 9a is a plan view of a solid state power source with frames according to an embodiment of the invention shown in FIG. 5a.

FIG. 10b is a side view of FIG. 10a.

DETAILED DESCRIPTION OF THE PREFERRED EMBODIMENTS

Figure 1:
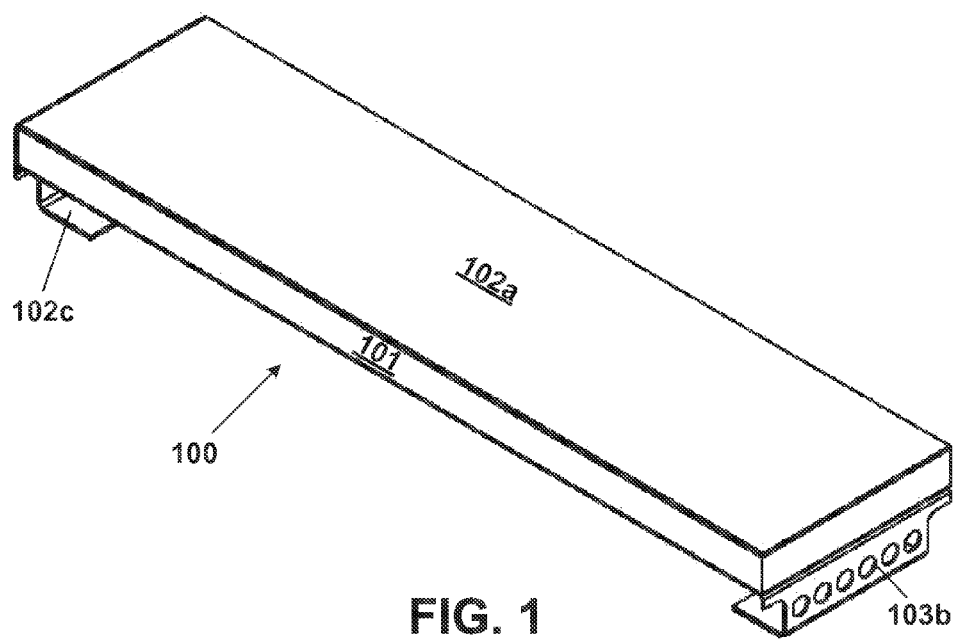
FIG. 1 is a top isometric view of a solid state power source with frames according to an embodiment of the invention.

Embodiments of the present invention are not limited to the particular methodology, compounds, materials, manufacturing techniques, uses, and applications described herein, as these may vary. It is also to be understood that the terminology used herein is used for the purpose of describing particular embodiments only, and is not intended to limit the scope of embodiments of the present invention. It must be noted that as used herein and in the appended claims, the singular forms "a," "an," and "the" include the plural reference unless the context clearly dictates otherwise. Thus, for example, a reference to "an element" is a reference to one or more elements, and includes equivalents thereof known to those skilled in the art. Similarly, for another example, a reference to "a step" or "a means" is a reference to one or more steps or means and may include sub-steps or subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Reference will now be made in detail to the preferred embodiments of the invention, examples of which are illustrated in the accompanying drawings. The invention may, however, be embodied in many different forms and should not be construed as being limited to the embodiments set forth herein; rather, these embodiments are provided so that this disclosure will be thorough and complete, and will fully convey the concept of the invention to those skilled in the art. In the drawings, the thicknesses of layers and regions are exaggerated for clarity. Like reference numerals in the drawings denote like elements.

Unless defined otherwise, all technical and scientific terms used herein have the same meanings as commonly understood by one of ordinary skill in the art to which this invention belongs. Preferred methods, techniques, devices and materials are described although any methods, techniques, devices, or materials similar or equivalent to those described may be used in the practice or testing of the present invention.

All patents and other publications discussed are incorporated herein by reference for the purpose of describing and disclosing, for example, the methodologies described in such publications that might be useful in connection with the present invention. These publications are provided solely for their disclosure prior to the filing date of the present application. Nothing in this regard should be construed as an admission that the inventors are not entitled to antedate such disclosure by virtue of prior invention or for any other reason.

Figure 2:
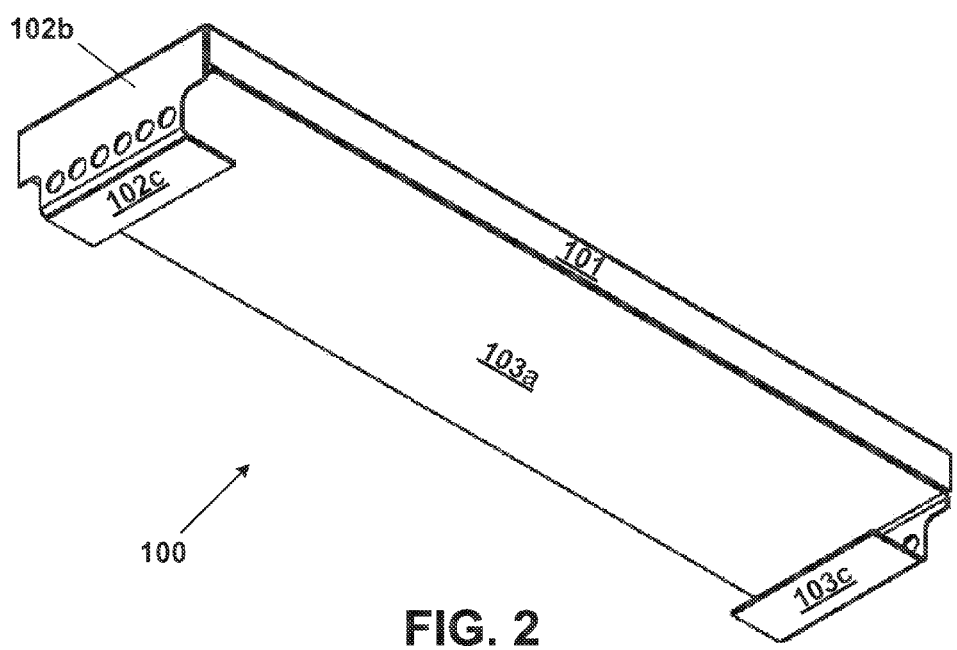
FIG. 2 is a bottom isometric view of a solid state power source with frames according to an embodiment of the invention.

FIGS. 1 and 2 are top and bottom isometric views of a solid state power source with frames according to an embodiment of the invention. As shown in FIGS. 1 and 2, a power source 100 for a solid state device can include, for example, a component 101 with an electrochemical cell with one side contacting a top frame portion 102a and another side contacting a bottom frame portion 103a that is completely separated from the top frame portion 102a. The bottom frame portion 103a can be, for example, connected to a bottom frame bonding portion 103c through a bottom frame extension portion 103b positioned between the bottom frame portion 103a and the bottom frame bonding portion 103c. The top frame portion 102a is, for example, connected to a top frame bonding portion 102c through a top frame extension portion 102b positioned between the top frame portion 102a and the top frame bonding portion 102c. The top frame extension portion 102b extends past the component 101 of the electrochemical cell. As shown in FIG. 2, the top frame bonding portion 102c and the bottom frame bonding portion 103c can both, for example, be on one side of component 101. The power source 100 in embodiments of the invention is preferably an electrochemical cell using rechargeable lithium based chemistry.

Figure 3:
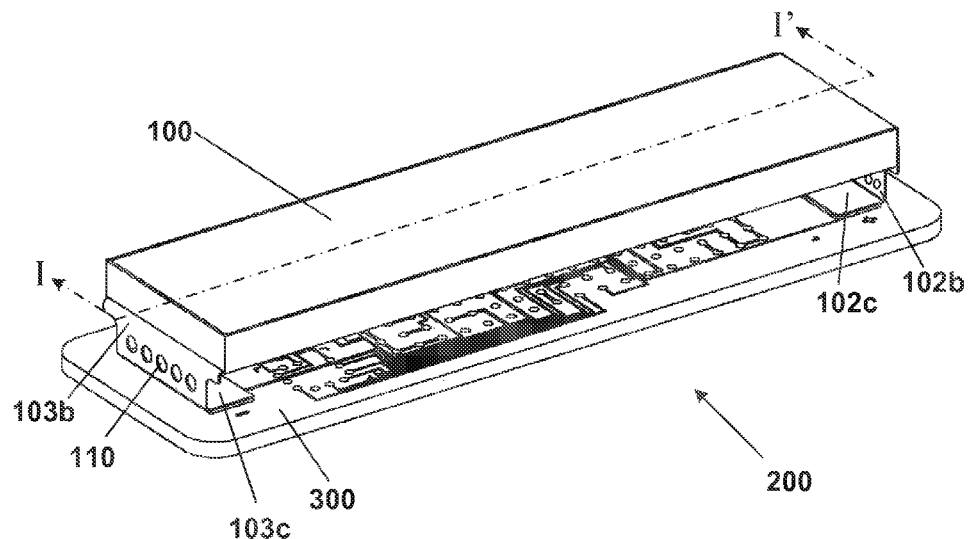
FIG. 3 is a top isometric view of a device including a solid state power source with frames attached to an electronic circuit according to an embodiment of the invention.

FIG. 3 is a top isometric view of a solid state power source with frames attached to an electronic circuit according to an embodiment of the invention. As shown in FIG. 3, an operational circuit 200 is manufactured, for example, when the power source 100 is electrically connected to an electronic circuit 300. The top frame bonding portion 102c is bonded to the electronic circuit 300 and the bottom frame bonding portion 103c is bonded to the electronic circuit 300. The openings 110 in the top frame extension portion 102b and the bottom frame extension portion 103b can reduce thermal transfer between power source 100 and the electronic circuit 300. Active electrical components can be integrated into the electronic circuit 300. Some exemplary electrical components that may be included in the electronic circuit 300 are illustrated in the circuit of the device(s) described in U.S. Pat. No. 5,987,352, "Minimally Invasive Implantable Device for Monitoring Physiologic Events" to Klein et al., incorporated herein by reference in its entirety. Further, the electrical components may include one or more of a capacitor, resistor, inductor, transmitter, antenna, or an actuator (such as a microelectromechanical device).

Figure 4:
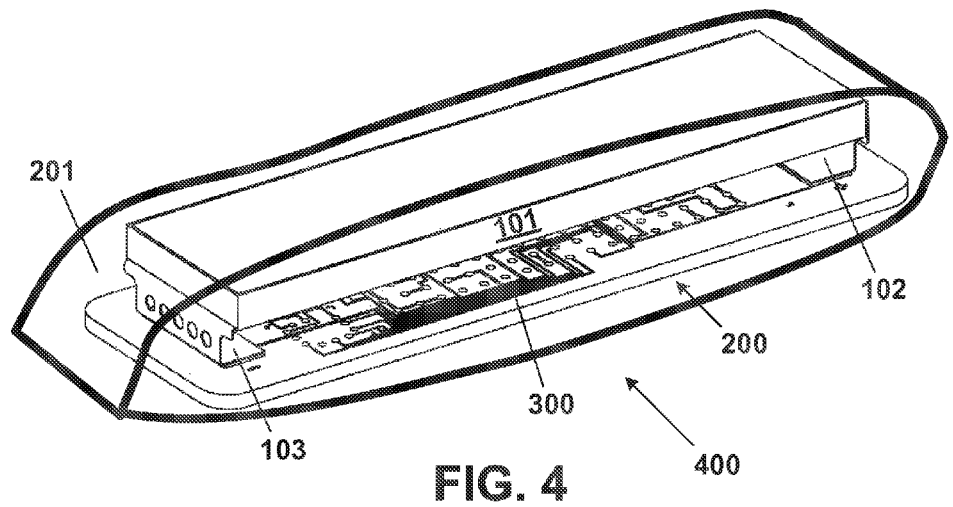
FIG. 4 is a top isometric view of a device having a solid state power source with frames attached to an electronic circuit according to an embodiment of the invention in which both the solid state power source and the electronic circuit are sealed in a hermetic enclosure of the device.

FIG. 4 is a top isometric view of a solid state power source with frames attached to an electronic circuit according to an embodiment of the invention in which both the solid state power source and the electronic circuit are sealed in a hermetic enclosure. As shown in FIG. 4, an implantable device 400 is, for example, an operational circuit 200 that is, for example, within a hermetic enclosure 201. More specifically, for example, a power source 100 including an electrochemical cell and frames 102 and 103 can, for example, be coupled to electronic circuit 300 and disposed within a hermetic enclosure 201. The operational circuit 200 can be inserted into a sheath and then a dry inert gas can be injected prior to the sheath being sealed to form a hermetic enclosure 201. Such a sheath can be, for example, a polymer that can be heat sealed or a metal that is laser welded. Any type of sealing method can be used that results in a hermetic enclosure 201 being both an air tight and body fluid tight.

An electrochemical cell having rechargeable lithium based chemistry is susceptible to degradation in ambient air and more so in moisture laden ambient air. In addition, an electrochemical cell having rechargeable lithium based chemistry can emit vapors that chemically or reactively attack an electronic circuitry. Although the electrochemical cell of the component 101 can, for example, use rechargeable lithium based chemistry, the electronic circuit 300 is not attacked by vapors emanating from electrochemical cell of the component 101 because the electrochemical cell is, for example, integrally encapsulated. Further, the electrochemical cell of the component 101, for example, is not susceptible to degradation due to ambient air or moisture laden ambient air because of the integral encapsulation of the electrolyte to the frames.

The integral encapsulation structure of the electrochemical cell in the component 101 that bonds to the frame enables mounting or attachment of the power source 100 to the electronic circuit 300 in an ambient environment. Subsequent to such bonding, testing of the operational circuit 200 can then be performed in ambient air. After an operational circuit 200 is inserted into a sheath in ambient air, the interior of the sheath can be purged with an inert gas and then sealed to form the hermetic enclosure 201 so as to result in an exemplary hermetically sealed implantable device 400.

Figure 5A:
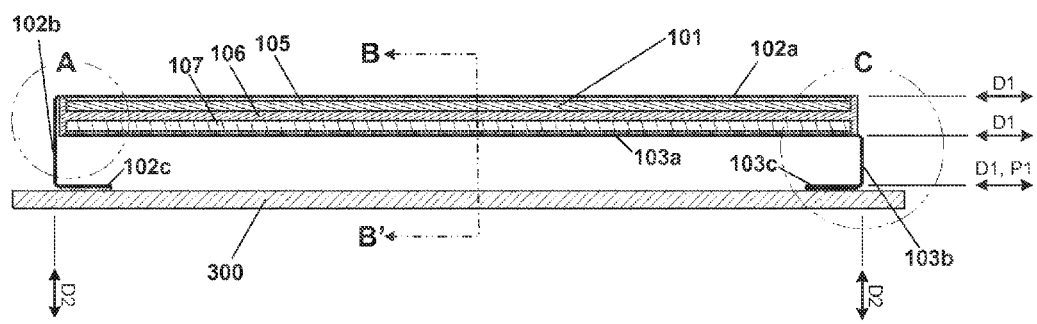
FIG. 5a is a cross-sectional view along lines I-I' shown in FIG. 3 of an embodiment of the invention having portions of the electrolyte layer between the frames function as an encapsulant.

FIG. 5a is a cross-sectional view along lines I-I' shown in FIG. 3 of an embodiment of the invention having portions of the electrolyte layer between the frames that can function as an encapsulant. As shown in FIG. 5a, an electrolyte layer 106 can be positioned between an anode 105 and cathode 107. The electrolyte layer 106 together with the top frame contacting portion 102a can, for example, completely surround the anode 105. The electrolyte layer 106 together with the bottom frame contacting portion 103a completely surround the cathode 107. The electrolyte 106 can be, for example, a polymer containing an electrolytic salt. Although layer 105 has been disclosed to be an anode and layer 107 has been described as a cathode for purposes of describing an embodiment of the invention, alternatively, layer 105 can be a cathode while layer 107 is an anode with the understanding that there is an appropriate polarity connection to the electronic circuit 300. In general, layers 105 and 107 can serve as posts of the electrochemical cell. The electrolyte layer may, for example, include materials as set forth in U.S. patent application Ser. No. 13/661,619 entitled "Fabrication of a High Energy Density Battery," which is hereby incorporated by reference in its entirety.

As also shown in FIG. 5a, the top frame contacting portion 102a and the bottom frame contacting portion 103a can be in the same direction D1. The top frame bonding portion 102c and the bottom frame bonding portion 103c can be, for example, in the same direction D1 as the top frame contacting portion 102a and bottom frame contacting portion 103a. Further, the top frame bonding portion 102c and the bottom frame bonding portion 103c can be, for example, in the same plane P1. The top frame extension portion 102b and the bottom frame extension portion 103b can be, for example, in a same direction D2 that is substantially perpendicular to the direction D1 of both the top frame bonding portion 102c and the bottom frame bonding portion 103c. The direction D2 of the top frame extension portion 102b and the bottom frame extension portion 103b is, for example, substantially perpendicular to the direction D1 of both the top frame bonding portion 102c and the bottom frame bonding portion 103c.

Figure 5B:
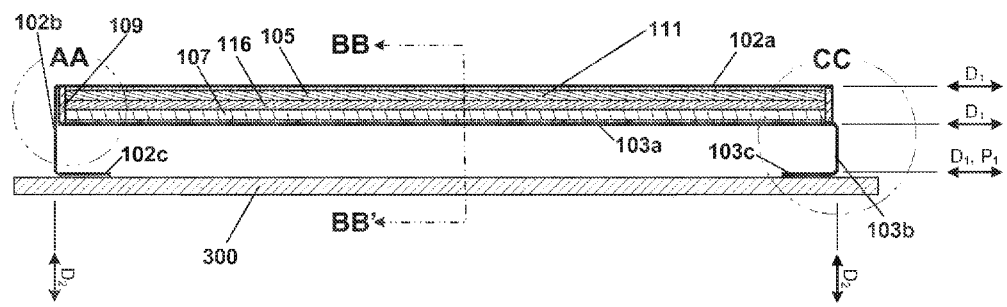
FIG. 5b is a cross-sectional view along lines I-I' shown in FIG. 3 of an embodiment of the invention having peripheral region between the frames functions as an encapsulant.

FIG. 5b is a cross-sectional view along lines I-I' shown in FIG. 3 of an embodiment of the invention having peripheral region between the frames that can function as an encapsulant. As shown in FIG. 5b, an electrolyte layer 116 is positioned between an anode 105 and cathode 107. The electrolyte 116 can be, for example, a polymer containing an electrolytic salt. An encapsulant region 109 can peripherally surrounds the electrolyte layer 116. The encapsulant region 109 together with the electrolyte layer 116 and the top frame contacting portion 102a can, for example, completely surround the anode 105. The encapsulant region 109 together with the electrolyte layer 116 and the bottom frame contacting portion 103a can completely surround the cathode 107. The encapsulant region 109 is, for example, a polymer that does not contain an electrolyte salt. The exemplary polymer of the encapsulant region 109 can have the same composition as the polymer in the electrolyte layer 106 or a different composition.

In the simplest form, the electrolyte layer may include one or more of the following, preferred polymers and derivatives thereof: Poly(vinylidene fluoride), poly(tetrafluoroethylene), polyacrylate, polyacrylonitrile, polyethylene, polypropylene, polyester, polyamide, polyimide, polyether, polycarbonate, polysulfone, and silicone. To provide these polymers with electrolytic properties, the polymers may be composited with at least one lithium salt, preferably selected from the group of lithium hexafluorophosphate, lithium hexafluoroantimonate, lithium tetrafluoroborate, lithium bis(trifluoromethylsulfonyl)imide, and lithium bis(fluorosulfonyl)imide. For example, electrolyte layer 106 may be composed of polyacrylonitrile, polysulfone, and lithium tetrafluoroborate while encapsulant region 109 may be composed only of polyacrylonitrile and polysulfone. In another example, electrolyte later 106 may be composed of polyacrylonitrile, polysulfone, and lithium tetrafluoroborate while encapsulant region 109 may consist of poly(tetrafluoroethylene).

As also shown in FIG. 5b, the top frame contacting portion 102a and the bottom frame contacting portion 103a are in the same direction D1. The top frame bonding portion 102c and the bottom frame bonding portion 103c are in the same direction D1 as the top frame contacting portion 102a and bottom frame contacting portion 103a. Further, the top frame bonding portion 102c and the bottom frame bonding portion 103c are, for example, in the same plane P1. The top frame extension portion 102b and the bottom frame extension portion 103b are in a same direction D2 that is substantially perpendicular to the direction D1 of both the top frame contacting portion 102a and the bottom frame contacting portion 103a. The direction D2 of the top frame extension portion 102b and the bottom frame extension portion 103b is, for example, substantially perpendicular to the direction D1 of both the top frame bonding portion 102c and the bottom frame bonding portion 103c.

Figure 6A:
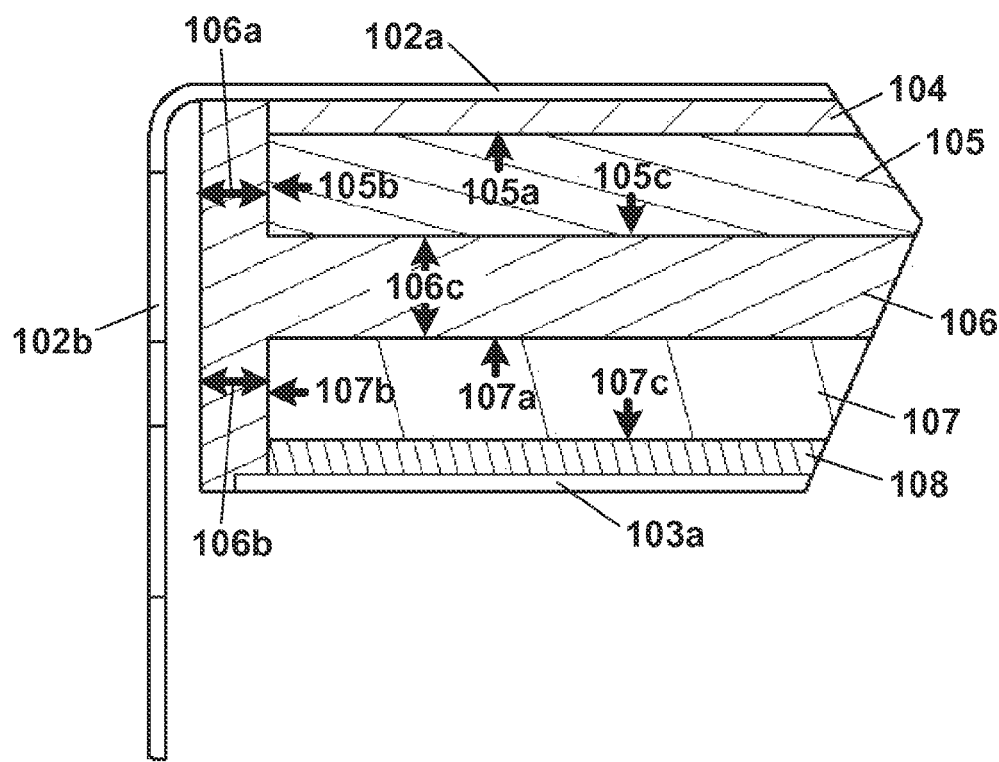

FIG. 6a is a detailed cross-sectional view of an embodiment at section A in FIG. 5a. As shown in FIG. 6a, an upper electrolyte layer portion 106a can be between an anode side 105b and the top frame extension portion 102b while a lower electrolyte layer portion 106b can be between a cathode side 107b and the top frame extension portion 102b. A middle electrolyte layer portion 106c can be positioned between a lower anode side 105c and an upper cathode side 107a. An upper conductive adhesive layer 104 can, for example, be positioned between the top frame contacting portion 102a and an upper anode side 105a. A lower conductive adhesive layer 108 can, for example, be positioned between the bottom frame contacting portion 103a and a lower cathode side 107c. In an alternative, the upper conductive adhesive layer 104 and the lower conductive adhesive layer 108 can be omitted such that the top frame contacting portion 102a is adhered to the upper anode side 105a and the bottom frame contacting portion 103a is adhered to the lower cathode side 107c. An electrical insulation film 112 can be positioned between the top frame extension portion 102b and cathode side 107b to prevent an undesired electrical affect between top frame extension portion 102b and cathode side 107b through the lower electrolyte layer portion 106b. The electrical insulation film 112 can be on at least one of the top frame extension portion 102b or the lower electrolyte layer portion 106b. For example, the insulating film 112 can be MgO.

Figure 6B:
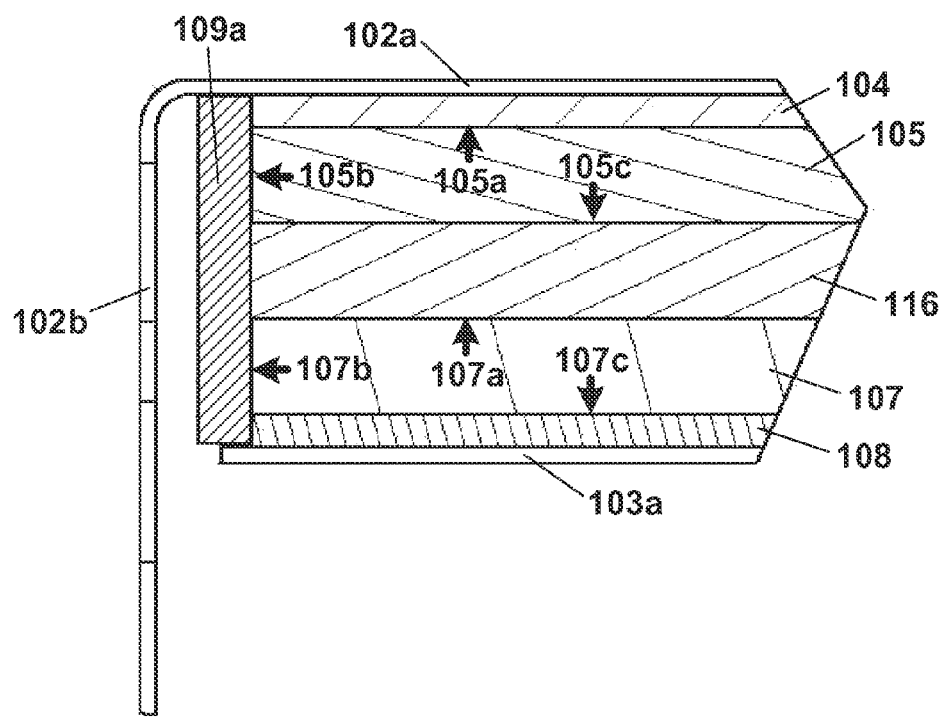
FIG. 6b is a detailed cross-sectional view of an embodiment at section AA in FIG. 5b.

FIG. 6b is a detailed cross-sectional view of an embodiment at section AA in FIG. 5b. As shown in FIG. 6b, an encapsulant region 109a can be between an anode side 105b and the top frame extension portion 102b and also can, for example, extend between a cathode side 107b and the top frame extension portion 102b. The electrolyte layer 116 can be positioned between a lower anode side 105c and an upper cathode side 107a. An upper conductive adhesive layer 104 can, for example, be positioned between the top frame contacting portion 102a and an upper anode side 105a. A lower conductive adhesive layer 108 can, for example, be positioned between the bottom frame contacting portion 103a and a lower cathode side 107c. In an alternative, the upper conductive adhesive layer 104 and the lower conductive adhesive layer 108 can be omitted such that the top frame contacting portion 102a is adhered to the upper anode side 105a and the bottom frame contacting portion 103a is adhered to the lower cathode side 107c.

Figure 7A:
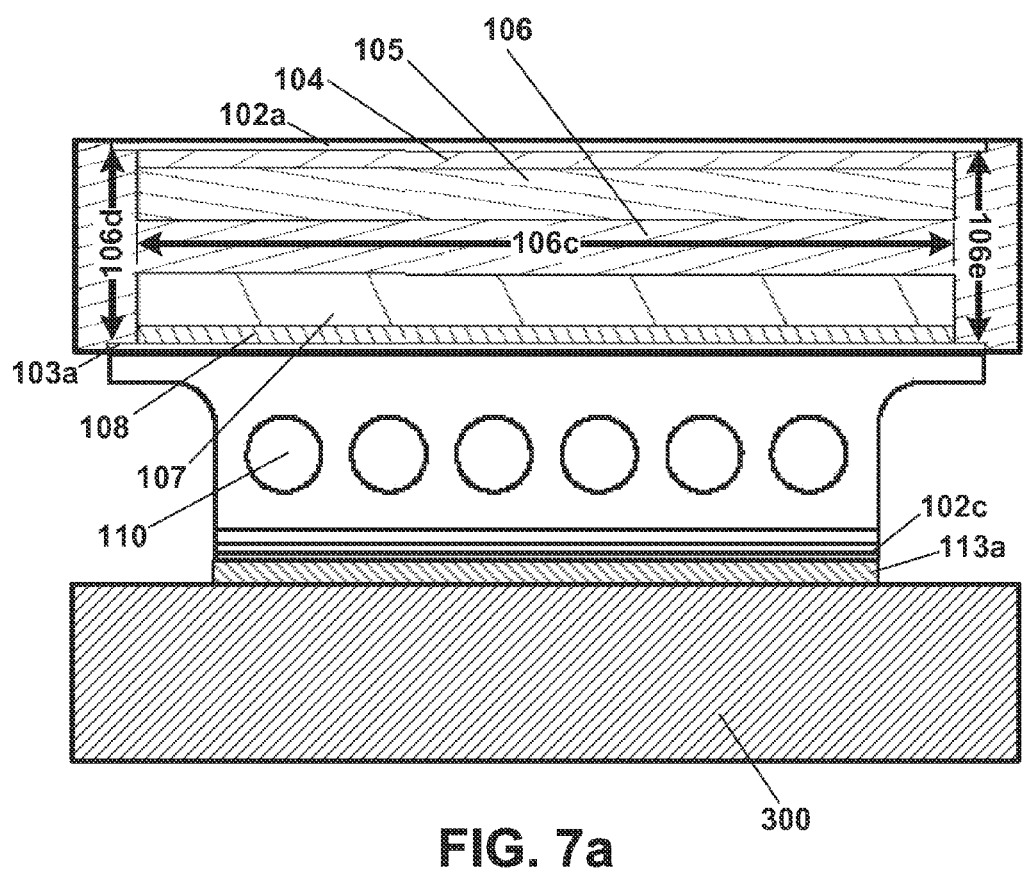

FIG. 7a is a cross-sectional view along lines B-B' of the embodiment in FIG. 5a. As shown in FIG. 7a, side electrolyte layer portions 106d and 106e are, for example, positioned between the top frame contacting portion 102a and the bottom frame contacting portion 103a. The side electrolyte layer portions 106d and 106e can, for example, extend beyond the top frame contacting portion 102a and the bottom frame contacting portion 103a. The middle electrolyte layer portion 106c can be positioned between the anode 105 and the cathode 107. The top frame bonding portion 102c can be electrically and mechanically connected to the electronic circuit 300 with a conductive connection adhesive 113a.

Figure 7B:
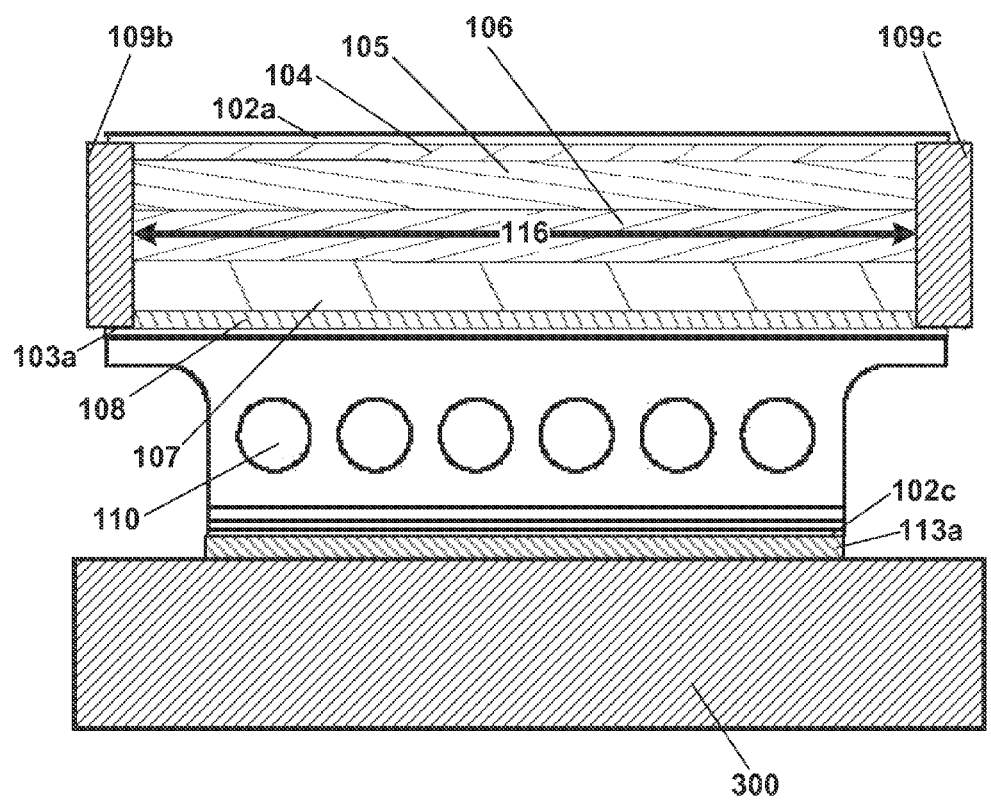
FIG. 7b a cross-sectional view along lines BB-BB' of the embodiment in FIG. 5b.

FIG. 7b is a cross-sectional view along lines BB-BB' of the embodiment in FIG. 5b. As shown in FIG. 7b, side encapsulant regions 109b and 109c can, for example, be positioned between the top frame contacting portion 102a and the bottom frame contacting portion 103a. The side encapsulant regions 109a and 109b can, for example, extend beyond the top frame contacting portion 102a and the bottom frame contacting portion 103a. The electrolyte layer 116 can be positioned between the anode 105 and the cathode 107. The top frame bonding portion 102c can be electrically and mechanically connected to the electronic circuit 300 with a conductive connection adhesive 113a.

Figure 8A:
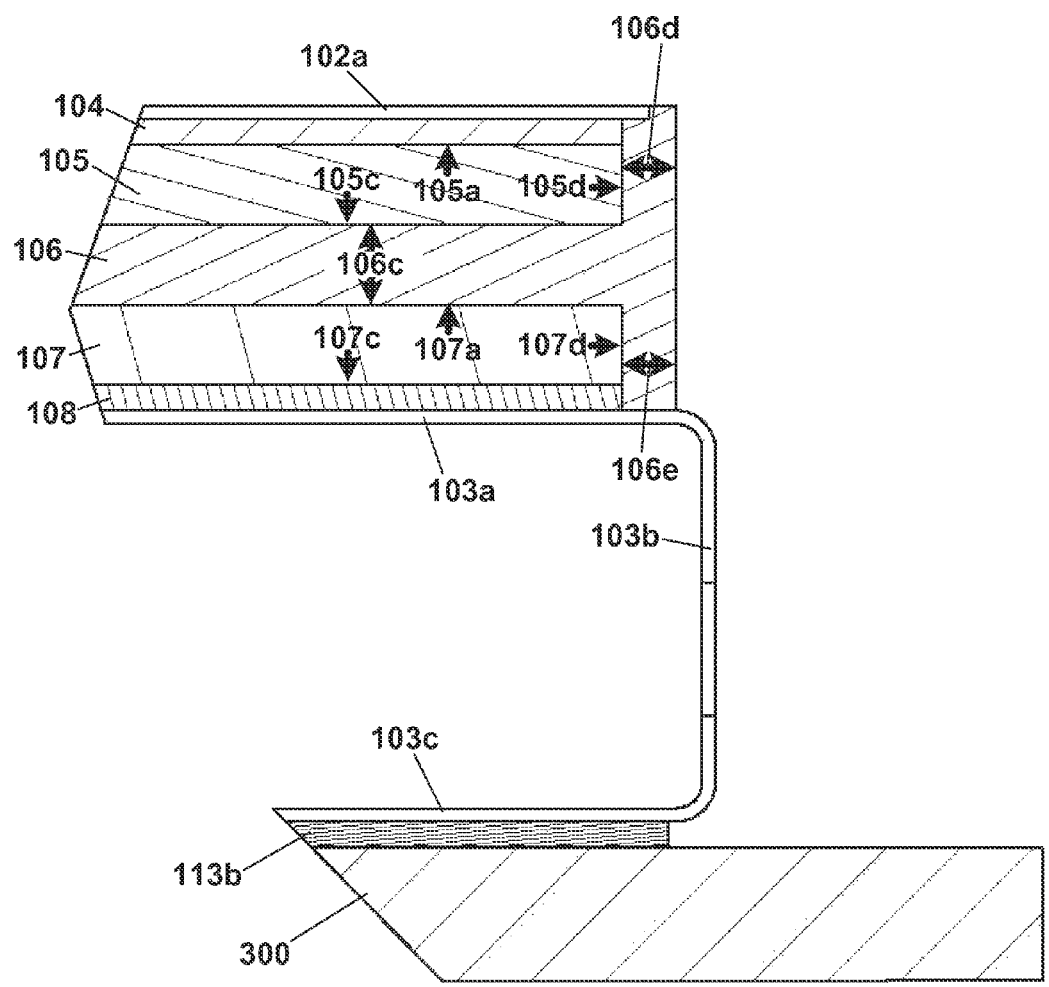

FIG. 8a is a detailed cross-sectional view of section C of the embodiment in FIG. 5a. As shown in FIG. 8a, an upper electrolyte layer portion 106d is, for example, at an anode side 105d and a lower electrolyte layer portion 106e is, for example, at a cathode side 107d. The middle electrolyte layer portion 106c can be positioned between a lower anode side 105c and an upper cathode side 107a. The upper electrolyte layer portion 106d and the lower electrolyte layer portion 106e can, for example, extend beyond the top frame contacting portion 102a. The bottom frame bonding portion 103c can, for example, be electrically and mechanically connected to the electronic circuit 300 with a conductive connection adhesive 113b.

Figure 8B:
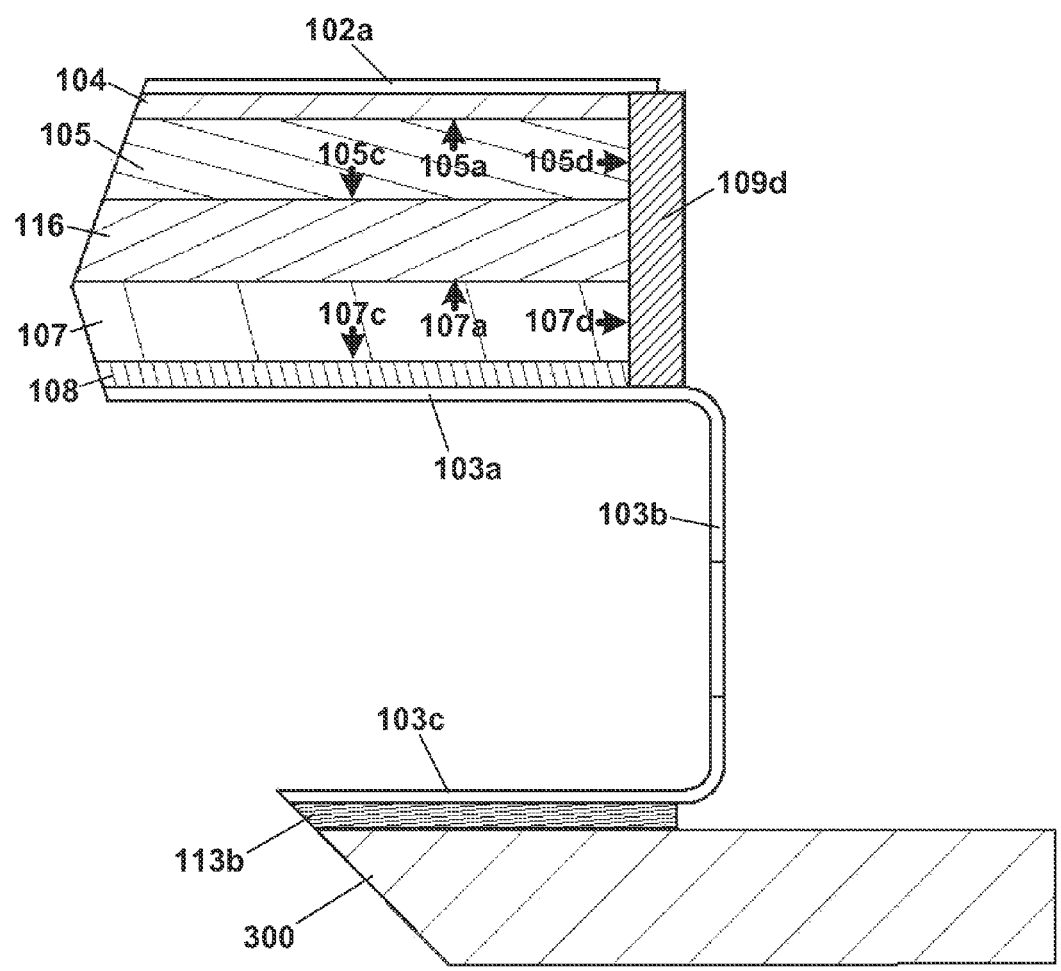
FIG. 8b is a detailed cross-sectional view of section CC of the embodiment in FIG. 5b.

FIG. 8b is a detailed cross-sectional view of section CC of the embodiment in FIG. 5b. As shown in FIG. 8b, a side encapsulant region 109d is, for example, at an anode side 105d and at a cathode side 107d. The electrolyte layer 116 can be positioned between a lower anode side 105c and an upper cathode side 107a. The side encapsulant region 109d can, for example, extend beyond the top frame contacting portion 102a. The bottom frame bonding portion 103c is, for example, electrically and mechanically connected to the electronic circuit 300 with a conductive connection adhesive 113b.

Figure 9A:
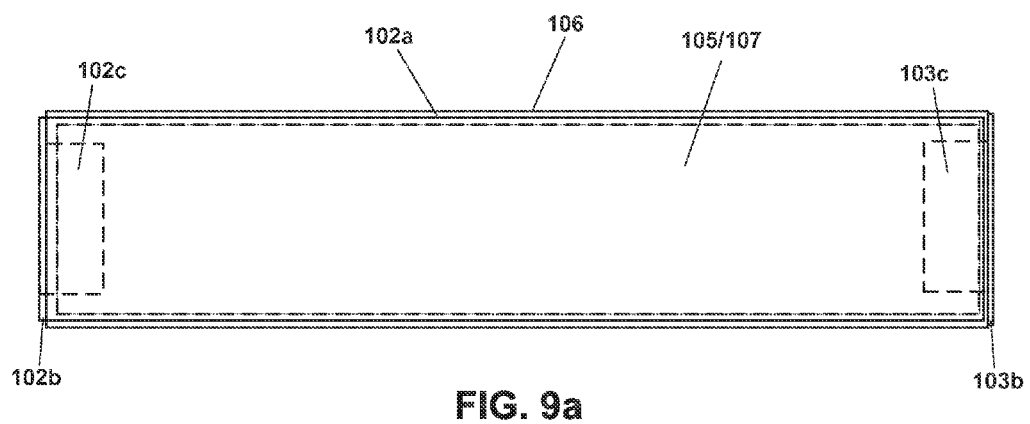

FIG. 9a is a plan view of a solid state power source with frames according to an embodiment of the invention shown in FIG. 5a. As shown in FIG. 9a, the electrolyte layer can extend beyond three sides of the top frame contacting portion 102a. The anode 105 and cathode 107 are, for example, within the sides of the top frame contacting portion 102a.

Figure 9B:
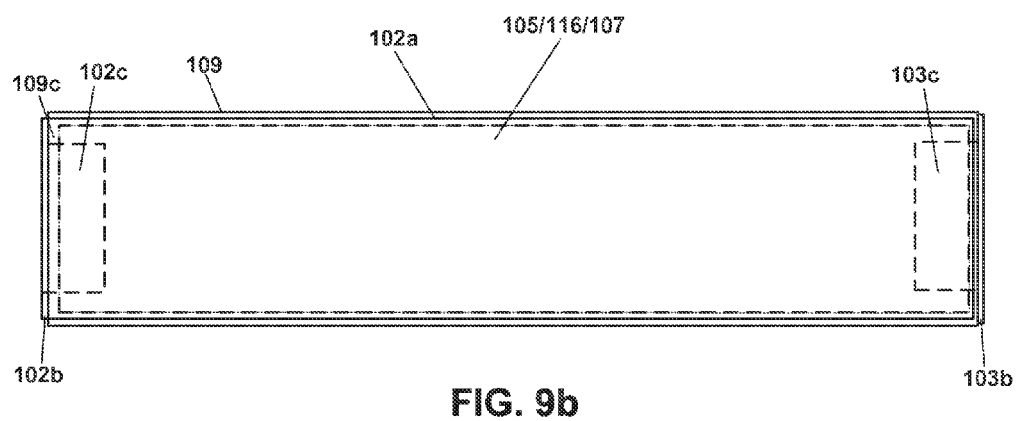
FIG. 9b is a plan view of a solid state power source with frames according to an embodiment of the invention shown in FIG. 5b.

FIG. 9b is a plan view of a solid state power source with frames according to an embodiment of the invention shown in FIG. 5b. As shown in FIG. 9b, the integral encapsulant region 109 extends beyond three sides of the top frame contacting portion 102a. The anode 105, electrolyte layer and cathode 107 are, for example, within the sides of the top frame contacting portion 102a.

Figure 10A:
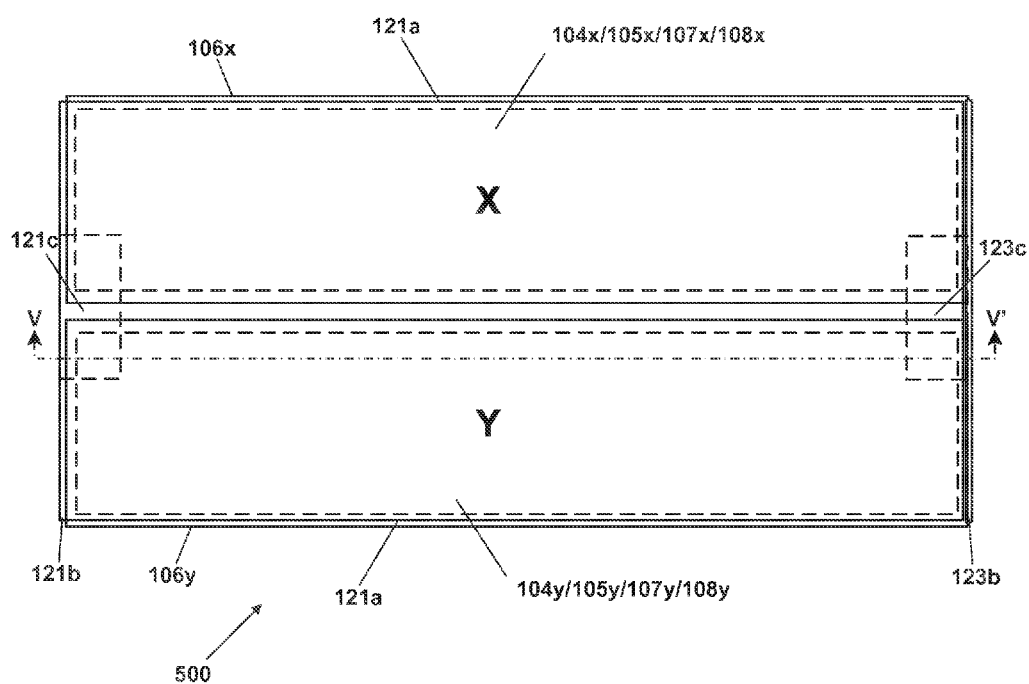
FIG. 10a is a plan view of first and second solid state power sources in parallel on same frames attached to an electronic circuit according to an embodiment of the invention.
Figure 10B:
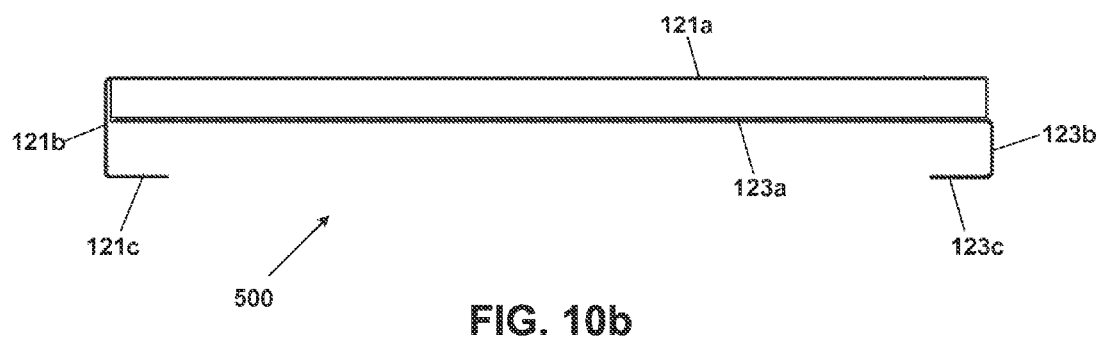

FIG. 10a is a plan view of first and second solid state power sources in parallel on same frames attached to an electronic circuit according to an embodiment of the invention. FIG. 10b is a side view of FIG. 10a. As shown in FIGS. 10a and 10b, a double cell power source 500 for a solid state device includes, for example, a first bare structure of an electrochemical cell X and a second bare structure of an electrochemical cell Y that are both, for example, positioned between a top frame contacting portion 121a and a bottom frame contacting portion 121c. The top frame contacting portion 121a is, for example, connected to a top frame bonding portion 121c through a top frame extension portion 121b. The bottom frame contacting portion 121c is, for example, connected to a bottom frame bonding portion 123c through a top frame extension portion 123b.

Figure 11:
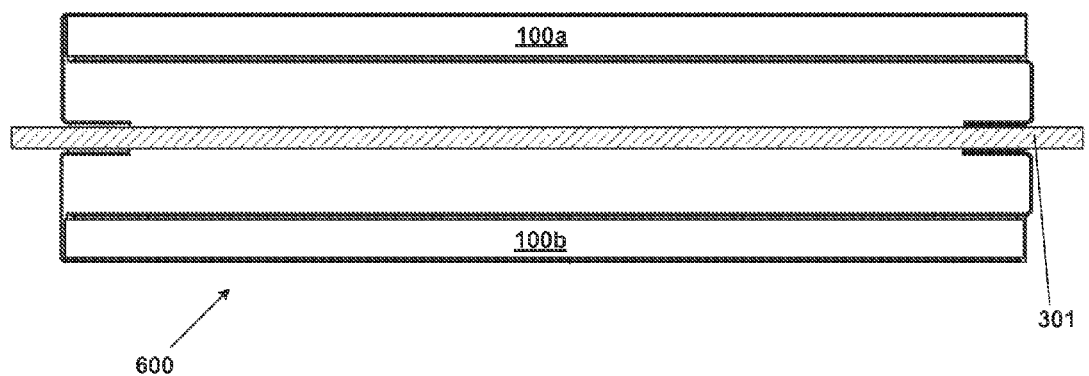
FIG. 11 is a side view of a first solid state power source with first frames attached to an electronic circuit and a second solid state power source with second frames attached to the same electronic circuit according to an embodiment of the invention.

FIG. 11 is a side view of a first solid state power source with first frames attached to an electronic circuit and a second solid state power source with second frames attached to the same electronic circuit according to an embodiment of the invention. As shown in FIG. 11, a dual power source architecture 600 for a solid state device includes, for example, a first power source 100a on one surface of the electronic circuit 301 and a second power source 100b on an opposite surface of the electronic circuit 301. Although the first and second power sources 100a and 100b are on opposite sides of the electronic circuit, the first and second power sources 100a and 100b can be electrically connected in parallel.

The embodiments and examples described above are exemplary only. One skilled in the art may recognize variations from the embodiments specifically described here, which are intended to be within the scope of this disclosure and invention. As such, the invention is limited only by the following claims. Thus, it is intended that the present invention cover the modifications of this invention provided that they come within the scope of the appended claims and their equivalents.

What is claimed is:

1. A device, comprising:
    an electronic circuit having a substrate with a first side and a second side;
    a first frame and a second frame;
    a first side encapsulant region and a second side encapsulant region positioned between the first and second frames;
    a first battery having a first pole layer, a first electrolyte layer and a second pole layer positioned between the first and second frames, and between the first and second side encapsulant regions,
    wherein the first and second frames electrically and mechanically contact the electronic circuit on the first side of the substrate.

2. The device according to claim 1, wherein the first electrolyte layer is a composite including an electrolyte salt and a first polymer, and the first and second side encapsulant regions include the first polymer.

3. The device according to claim 2, further comprising third and fourth side encapsulant regions positioned between the first and second contact portions such that the first, second, third and fourth encapsulant regions encircle the first and second poles.

4. The device according to claim 1, wherein the first electrolyte layer is a composite including an electrolyte salt and a first polymer and the first and second side encapsulant regions include a second polymer different than the first polymer.

5. The device according to claim 4, further comprising third and fourth side encapsulant regions positioned between the first and second frames such that the first, second, third and fourth encapsulant regions encircle the first and second poles.

6. The device according to claim 1, wherein the first frame is attached to the first pole layer with a first conductive adhesive layer and the second frame is attached to the second pole layer with a second conductive adhesive layer.

7. The device according to claim 1, further comprising;
    a hermetic enclosure surrounding the first battery and substrate.

8. The device according to claim 1, further comprising:
    a first conductive connection adhesive electrically and mechanically connecting the first frame to the electronic circuit on the first side of the substrate and a second conductive connection adhesive electrically and mechanically connecting the second frame to the electronic circuit on the first side of the substrate.

9. The device according to claim 1, further comprising
    a second battery having a third pole layer, a second electrolyte layer and a fourth pole layer positioned between third and fourth frames, and between third and fourth side encapsulant regions.

10. The device according to claim 9, further comprising:
    a third conductive connection adhesive electrically and mechanically connecting the third frame to the electronic circuit on the second side of the substrate and a fourth conductive connection adhesive electrically and mechanically connecting the fourth frame to the electronic circuit on the second side of the substrate.

* * * * *